US009125804B2

(12) United States Patent
Webb et al.

(10) Patent No.: US 9,125,804 B2
(45) Date of Patent: Sep. 8, 2015

(54) PHARMACEUTICAL COMPOSITION COMPRISING BOTULINUM, A NON IONIC SURFACTANT, SODIUM CHLORIDE AND SUCROSE

(75) Inventors: Paul Webb, Wrexham (GB); Mary White, Wrexham (GB); Julie Partington, Wrexham (GB)

(73) Assignee: IPSEN BIOPHARM LIMITED, Wrexham (GB)

( * ) Notice: Subject to any disclaimer, the term of this patent is extended or adjusted under 35 U.S.C. 154(b) by 984 days.

(21) Appl. No.: 11/632,156

(22) PCT Filed: Jul. 6, 2005

(86) PCT No.: PCT/GB2005/002653
§ 371 (c)(1),
(2), (4) Date: Sep. 4, 2007

(87) PCT Pub. No.: WO2006/005910
PCT Pub. Date: Jan. 19, 2006

(65) Prior Publication Data
US 2008/0050352 A1     Feb. 28, 2008

(30) Foreign Application Priority Data
Jul. 12, 2004   (GB) .................................. 0415491.0

(51) Int. Cl.
| A61K 9/08 | (2006.01) |
| A61K 9/19 | (2006.01) |
| A61K 38/48 | (2006.01) |
| A61K 47/26 | (2006.01) |
| A61K 9/00 | (2006.01) |

(52) U.S. Cl.
CPC .................. *A61K 9/0019* (2013.01); *A61K 9/19* (2013.01); *A61K 38/4886* (2013.01); *A61K 38/4893* (2013.01); *A61K 47/26* (2013.01)

(58) Field of Classification Search
CPC . A61K 38/4893; A61K 9/0019; A61K 47/26; A61K 2800/91; A61K 47/183; A61K 9/107; A61K 9/19; A61K 9/08; A61M 5/178; A61Q 19/00
See application file for complete search history.

(56) References Cited

U.S. PATENT DOCUMENTS

| 5,512,547 | A | 4/1996 | Johnson et al. .................. 514/21 |
| 5,733,873 | A * | 3/1998 | Osterberg et al. ............ 514/13.7 |
| 5,756,468 | A | 5/1998 | Johnson et al. ................. 514/21 |
| 7,579,010 | B2 * | 8/2009 | Hunt .......................... 424/236.1 |
| 2002/0028216 | A1 | 3/2002 | Donovan ....................... 424/236 |
| 2002/0197278 | A1 | 12/2002 | Allison ......................... 424/239 |
| 2003/0118598 | A1 | 6/2003 | Hunt ............................ 424/184 |
| 2003/0138437 | A1 | 7/2003 | Hunt ............................ 424/184 |
| 2004/0033241 | A1 | 2/2004 | Donovan ....................... 424/239 |
| 2004/0086532 | A1 | 5/2004 | Donovan ....................... 424/239 |

FOREIGN PATENT DOCUMENTS

| RU | 2206337 | 6/2003 |
| WO | WO96/11699 | 4/1996 |
| WO | WO97/35604 | 10/1997 |
| WO | WO99/37326 | 7/1999 |
| WO | 01/37656 A2 | 5/2001 |
| WO | WO01/58472 | 8/2001 |
| WO | WO2004/006954 | 1/2004 |
| WO | WO2004/019905 | 3/2004 |
| WO | WO2004/043430 | 5/2004 |
| WO | 2005/007185 | 1/2005 |
| WO | WO2006/013357 | 2/2006 |
| WO | WO2006/013370 | 2/2006 |

OTHER PUBLICATIONS

Tween® 80. Product Information from Sigma-Aldrich. May 2006, p. 1-2.*
Tobio et al, Pharmaceutical Research, vol. 16, No. 5, 1999, pp. 682-688, A Novel System Based on a Poloxamer/PLGA Blend as a . . . .
Goodnough et al., Applied & Envir. Microbiology, vol. 58, No. 10, Oct. 1992, pp. 3426-3426, Stabilization of Botulinum Toxin . . . .
Curent Topics in Microbiology . . . , vol. 195, 1995, pp. 151-154, Chapter 5, Purification of Clostridial Neurotoxins.
DasGupta, CRC Handbook . . . , 1995, pp. 25-56, Microbial Food Toxicants: Clostridium Botulinum Toxins.
Thomas Österberg et al., Development of a Freeze-Dried Albumin-Free Formulation of Recombinant Factor VIII SQ, Pharmaceutical Research, vol. 14, No. 7, 1997, pp. 892-898.
Y. Sagane et al., "Botulinum Toxin Complex: A Delivery Vehicle of Botulinum Neurotoxin Traveling Digestive Tract," Structure and Function of Food Engineering, Chapter 6; 2012, http://dx.doi.org/10.5772/46023; 14 pages.
Tan Weifeng at at., "Progress in Application of Botulinum toxin type A in Plastic Surgery", Chinese Journal of Medical Aesthetic and Comsmetology, vol. 9, No. 3, Jun. 2003.
Chi et al, "Physical Stability of Proteins in Aqueous Solution: Mechanism and Driving Forces in Nonnatice Protein Aggregation", Pharmaceutical Research, vol. 20, No. 9, Sep. 2003.
Brin, Archives of Ophthalmology, 2003, vol. 121, No. 11, pp. 1661-1662.
Haemophilia, "Loss of factor VIII activity during storage in PVC containers due to adsorption", vol. 6, No. 2, pp. 89-92, Mar. 2000.
Notice of Opposition mailed Jul. 9, 2014 against counterpart European patent application.

* cited by examiner

*Primary Examiner* — Taeyoon Kim
(74) *Attorney, Agent, or Firm* — Hunton & Williams LLP

(57) ABSTRACT

The invention relates to a solid or liquid pharmaceutical composition comprising botulinum neurotoxin complex (type A, B, C, D, E, F or G) or high purity botulinum neurotoxin (type A, B, C, D, E, F or G), and a surfactant. In particular the invention relates to a solid or liquid pharmaceutical composition comprising a crystalline agent.

4 Claims, No Drawings

PHARMACEUTICAL COMPOSITION COMPRISING BOTULINUM, A NON IONIC SURFACTANT, SODIUM CHLORIDE AND SUCROSE

This is a national stage of PCT/GB05/002653 filed Jul. 6, 2005 and published in English.

The invention relates to a pharmaceutical composition containing botulinum neurotoxin.

The presently most used botulinum neurotoxin is botulinum neurotoxin type A. This neurotoxin is produced during fermentation in the presence of *Clostridium botulinum* strains. Botulinum neurotoxin type A complexes (which include botulinum neurotoxin type A and at least another non-toxic protein) are active principles widely used in modern medicine. An example of a pharmaceutical composition based on such a complex is the product Dysport® currently sold by the company of the Applicants. Among the most common medical indications for which a botulinum neurotoxin type A complex could be used, one could mention the treatment of a number of muscle disorders (e.g. blepharospasm, hemifacial spasm, torticollis, spasticity, tension headache, back pain or wrinkles), as well as other disorders such as migraine. Alternatively, high purity botulinum toxin (i.e. botulinum neurotoxin free from its complexing non-toxic proteins) may replace the corresponding botulinum toxin complex as disclosed in PCT applications WO 96/11699 or WO 97/35604.

Currently, the marketed botulinum neurotoxin compositions contain human serum albumin. However, some concerns have been expressed about albumin (see e.g. in PCT application WO 01/58472). For this reason, the pharmaceutical industry is now considering to find alternative stabilising agents to albumin by other stabilising agents in pharmaceutical compositions.

A possible solution is disclosed in PCT patent application WO 01/58472. In this document, albumin is replaced by a polysaccharide, i.e. a polymer of more than two saccharide molecule monomers, which plays the role of the stabiliser in the botulinum neurotoxin composition.

An alternative solution is the one described in PCT patent application WO 97/35604 or U.S. Pat. Nos. 5,512,547 and 5,756,468. In these documents, it is disclosed that pure botulinum neurotoxin (i.e. botulinum neurotoxin free from its complexing non-toxic proteins) can be stabilised by trehalose.

The Applicant has unexpectedly discovered that a surfactant possesses sufficient stabilising effects to replace albumin, the polysaccharide of PCT patent application WO 01/58472 or the trehalose of PCT patent application WO 97/35604 in botulinum neurotoxin compositions.

The invention therefore pertains to the use of a surfactant for stabilising a solid or liquid pharmaceutical composition that contains as active principle a botulinum toxin.

By botulinum toxin should be understood a naturally occurring botulinum toxin or any recombinantly produced botulinum toxin.

By naturally occurring botulinum toxin should be understood either a high purity botulinum neurotoxin derived from *Clostridium* spp or a botulinum neurotoxin complex derived from *Clostridium* spp.

By high purity botulinum neurotoxin (type A, B, C, D, E, F or G) is meant, in the present application, botulinum neurotoxin (type A, B, C, D, E, F or G) outside from complexes including at least another protein. In other words, a high purity botulinum neurotoxin (type A, B, C, D, E, F or G) does not contain significant quantities of any other *Clostridium* spp derived protein than botulinum neurotoxin (type A, B, C, D, E, F or G).

Preferably, according to the present invention, botulinum neurotoxin complexes and high purity botulinum neurotoxins will be selected from the group consisting of botulinum neurotoxin complex and high purity botulinum neurotoxin of type A, botulinum neurotoxin complex and high purity botulinum neurotoxin of type B and botulinum neurotoxin complex and high purity botulinum neurotoxin of type F. More preferably, botulinum neurotoxin complexes and high purity botulinum neurotoxins will be selected from the group consisting of botulinum neurotoxin complex and high purity botulinum neurotoxin of type A and botulinum neurotoxin complex and high purity botulinum neurotoxin of type F. More particularly, botulinum neurotoxin complexes and high purity botulinum neurotoxins will be botulinum neurotoxin complexes and high purity botulinum neurotoxins of type A.

By type A botulinum neurotoxin should be understood any botulinum toxin of type A, and notably botulinum neurotoxins of type A1, A2 or A3. The same applies mutatis mutandis to the other serotypes of toxins.

The high purity botulinum neurotoxin (type A, B, C, D, E, F or G) used according to the invention or contained in the above described pharmaceutical compositions can easily be obtained from the corresponding botulinum neurotoxin complex, for example as explained in Current Topics in Microbiology and Immunology (1995), 195, p. 151-154. High purity *Clostridium botulinum* toxin (type A, B, C, D, E, F or G) is obtained, for example, by purification of an adequate fermentation medium (for example, an enriched meat media broth containing *Clostridium Botulinum* and left for fermentation—this broth may be, for example, the one described in Current Topics in Microbiology and Immunology (1995), 195, p. 150 and DasGupta, "*Microbial food toxicants. Clostridium botulinum toxins. CRC handbook of foodborne diseases of biological origin*", CRC Boca Raton, p. 25-56). When including high purity botulinum neurotoxin in a composition according to the instant invention, the purity degree of the toxin should preferably be higher than 80%, more preferably higher than 90 or 95% and in a more particularly preferred manner higher than 98% or 99%. It can be assessed, for example, by using the purity assay described in the present application.

The instant invention also relates to a solid or liquid pharmaceutical composition comprising:

(a) a botulinum toxin, and
(b) a surfactant.

According to a particular variant of the invention, the pharmaceutical composition will be a solid pharmaceutical composition and will essentially consist of:

(a) a botulinum toxin, and
(b) a surfactant.

According to another particular variant of the invention, the pharmaceutical composition will be a liquid pharmaceutical composition and will essentially consist of:

(a) a botulinum toxin,
(b) a surfactant, and
(c) water.

In the abovementioned pharmaceutical compositions, the surfactant will be such that it stabilises the botulinum toxin.

A solid pharmaceutical composition according to the invention can be obtained for example by lyophilising a sterile water solution containing the components (a) and (b) as mentioned previously. A liquid pharmaceutical composition according to the invention will be obtained by mixing the solid (e.g. lyophilised) mixture of components (a) and (b) with sterile water.

According to the invention, the concentrations of said components (a) and (b) in the solution to be lyophilised or the liquid pharmaceutical composition will preferably be as follows:

the solution will contain from 50 to 10,000 LD50 units of botulinum neurotoxin complex (type A, B, C, D, E, F or G) or high purity botulinum neurotoxin (type A, B, C, D, E, F or G) per ml of solution, preferably [the solution will contain] from 50 to 3,000 LD50 units of botulinum neurotoxin complex (type A, B, C, D, E, F or G) or high purity botulinum neurotoxin (type A, B, C, D, E, F or G) per ml of solution, more preferably from 100 to 2,500 LD50 units of botulinum neurotoxin complex (type A, B, C, D, E, F or G) or high purity botulinum neurotoxin (type A, B, C, D, E, F or G) per ml of solution and most preferably from 100 to 2,000 LD50 units of botulinum neurotoxin complex (type A, B, C, D, E, F or G) or high purity botulinum neurotoxin (type A, B, C, D, E, F or G) per ml of solution;

the concentration of surfactant will be from above critical micellar concentration to a concentration of 1% v/v, and notably from about 0.005% to 0.02% v/v in the case of polysorbate 80.

Preferably, the surfactant will be a non-ionic surfactant. Non-ionic surfactants include notably polysorbates and block copolymers like poloxamers (i.e. copolymers of polyethylene and propylene glycol). According to a preferred variant of the invention, the surfactant will be a polysorbate. More preferably, a polysorbate included in a composition according to the instant invention will have a mean polymerisation degree of from 20 to 100 monomer units (preferably about 80), and may for example be polysorbate 80. Preferably also, the polysorbate should be vegetable-derived.

According to a preferred execution mode of the invention, the solid or liquid pharmaceutical composition will also contain a crystalline agent.

By crystalline agent is meant an agent which, inter alia, would maintain a mechanically strong cake structure to lyophilised botulinum neurotoxin complex (type A, B, C, D, E, F or G) or high purity botulinum neurotoxin (type A, B, C, D, E, F or G). When included in solid formulations, crystalline agents also have a bulking effect. Crystalline agents notably include sodium chloride. Contrarily to what was taught in the prior art (see e.g. Goodnough, M. C. and Johnson, E. A., *Applied and Environmental Microbiology* (1992), 58(10), 3426-3428), the use of sodium chloride for this type of compositions further improves the stability of the botulinum toxin composition.

According to yet another preferred execution mode of the invention, the solid or liquid pharmaceutical composition will also contain a buffer to maintain pH from 5.5 to 7.5.

The buffer can be any buffer able to maintain the adequate pH. Preferably, the buffer for compositions according to the invention will be chosen from the group consisting of succinate and an amino acid like histidine. In particular, the buffer will be histidine. Preferably, the pH will be at least equal to 5.5 or 5.8, and most preferably at least equal to 6.0 or 6.5. Preferably also, the pH will be equal to or less than 7.5 or 7.0, more preferably equal to or less than 6.8.

Preferably, the solid or liquid pharmaceutical composition of the invention may also contain a disaccharide.

The disaccharide used in compositions according to the invention will preferably be chosen from the group consisting of sucrose, trehalose, mannitol and lactose. The disaccharide used in compositions according to the invention will more preferably be chosen from the group consisting of sucrose and trehalose. In particular, the disaccharide used in compositions according to the invention will be sucrose. Preferably, the disaccharide will be present in the pharmaceutical compositions of the instant invention, particularly when the compositions are in a solid form.

The instant invention therefore notably relates to a solid or liquid pharmaceutical composition comprising:
(a) botulinum neurotoxin complex (type A, B, C, D, E, F or G) or high purity botulinum neurotoxin (type A, B, C, D, E, F or G),
(b) a surfactant,
(c) a crystalline agent,
(d) a buffer to maintain pH between 5.5 to 7.5.

Preferably, a disaccharide will also be included in the pharmaceutical compositions according to the present invention, especially when they are in a solid form.

According to this variant of the invention, a solid pharmaceutical composition can be obtained by lyophilising a sterile water solution containing the components (a) to (d) as mentioned previously. A liquid pharmaceutical composition according to the invention will be obtained by mixing a solid (e.g. lyophilized) mixture of said components (a) to (d) with sterile water.

According to the invention, the concentrations of said components (a) to (d) in the solution to be lyophilised or the liquid pharmaceutical composition will preferably be as follows:

the solution will contain from 50 to 10,000 LD50 units of botulinum neurotoxin complex (type A, B, C, D, E, F or G) or high purity botulinum neurotoxin (type A, B, C, D, E, F or G) per ml of solution, preferably [the solution will contain] from 50 to 3,000 LD50 units of botulinum neurotoxin complex (type A, B, C, D, E, F or G) or high purity botulinum neurotoxin (type A, B, C, D, E, F or G) per ml of solution, more preferably from 100 to 2,500 LD50 units of botulinum neurotoxin complex (type A, B, C, D, E, F or G) or high purity botulinum neurotoxin (type A, B, C, D, E, F or G) per ml of solution and most preferably from 100 to 2,000 LD50 units of botulinum neurotoxin complex (type A, B, C, D, E, F or G) or high purity botulinum neurotoxin (type A, B, C, D, E, F or G) per ml of solution;

the concentration of surfactant will be from above critical micellar concentration to a concentration of 1% v/v, and notably from about 0.005% to 0.02% v/v in the case of polysorbate 80;

the concentration of crystalline agent will be from 0.1 to 0.5 M, more preferably from 0.1 to 0.4 M, notably about 0.15 to 0.3 M; and the concentration of buffer will be from 1 to 50 mM, more preferably from 5 to 20 mM, notably about 10 mM.

As mentioned earlier, the solid or liquid pharmaceutical formulation according to the invention may contain a disaccharide. In that case, the concentration of disaccharide in the solution to be lyophilised/the liquid pharmaceutical composition will be for example from 5 to 50 mM, preferably from 5 to 25 mM, more preferably from 10 to 20 mM, and notably about 11.7 mM.

According to a preferred execution mode of the invention, the mixture of the different components of the pharmaceutical composition (i.e. botulinum neurotoxin complex (type A, B, C, D, E, F or G) or high purity botulinum neurotoxin (type A, B, C, D, E, F or G), the surfactant and the optional excipients such as the crystalline agent, the buffer or the disaccharide) is lyophilised. The solid compositions thus obtained, which are also part of this invention, should preferably be stable for at least 12 months, more preferably for at least 18 months and in a more particularly preferred manner for at least 24 or even 36 months.

A composition according to the invention is considered stable during a certain period of time if at least 70% of the initial toxicity, as evaluated by assessing the $LD_{50}$ in mice or by any method validated with respect to the $LD_{50}$ mouse assay (i.e. a method allowing a conversion of its results into $LD_{50}$ units), is maintained over said period of time (cf. the part entitled "mouse toxicity assay" concerning the $LD_{50}$ mouse assay). Pharmaceutical compositions according to the invention can be used for preparing medicaments intended to treat a disease/a condition/a syndrome chosen from the following:

ophtalmological disorders selected from the group consisting of blepharospasm, strabismus (including restrictive or myogenic strabismus), amblyopia, oscillopsia, protective ptosis, therapeutic ptosis for corneal protection, nystagmus, estropia, diplopia, entropion, eyelid retraction, orbital myopathy, heterophoria, concomitant misalignment, nonconcomitant misalignment, primary or secondary esotropia or exotropia, internuclear ophthalmoplegia, skew deviation, Duane's syndrome and upper eyelid retraction;

movement disorders including hemifacial spasm, torticollis, spasticity of the child or of the adult (e.g. in cerebral palsy, post-stroke, multiple sclerosis, traumatic brain injury or spinal cord injury patients), idiopathic focal dystonias, muscle stiffness, Writer's cramp, hand dystonia, VI nerve palsy, oromandibular dystonia, head tremor, tardive dyskinesia, tardive dystonia, occupational cramps (including musicians' cramp), facial nerve palsy, jaw closing spasm, facial spasm, synkinesia, tremor, primary writing tremor, myoclonus, stiff-person-syndrome, foot dystonia, facial paralysis, painful-arm-and-moving-fingers-syndrome, tic disorders, dystonic tics, Tourette's syndrome, neuromyotonia, trembling chin, lateral rectus palsy, dystonic foot inversion, jaw dystonia, Rabbit syndrome, cerebellar tremor, III nerve palsy, palatal myoclonus, akasthesia, muscle cramps, IV nerve palsy, freezing-of-gait, extensor truncal dystonia, post-facial nerve palsy synkinesis, secondary dystonia, Parkinson's disease, Huntington's chorea, epilepsy, off period dystonia, cephalic tetanus, myokymia and benign cramp-fasciculation syndrome;

otorhinolaryngological disorders including spasmodic dysphonia, hypersalivation, sialorrhoea, otic disorders, hearing impairment, ear click, tinnitus, vertigo, Meniere's disease, cochlear nerve dysfunction, stuttering, cricopharyngeal dysphagia, bruxism, closure of larynx in chronic aspiration, vocal fold granuloma, ventricular dystonia, ventricular dysphonia, mutational dysphonia, trismus, snoring, voice tremor, aspiration, tongue protrusion dystonia, palatal tremor, deep bite of lip and laryngeal dystonia;

gastrointestinal disorders including achalasia, anal fissure, constipation, temperomandibular joint dysfunction, sphincter of Oddi dysfunction, sustained sphincter of Oddi hypertension, intestinal muscle disorders, puborectalis syndrome, anismus, pyloric spasm, gall bladder dysfunction, gastrointestinal or oesophageal motility dysfunction, diffuse oesophageal spasm and gastroparesis;

urogenital disorders including detrusor sphincter dyssynergia, detrusor hyperreflexia, neurogenic bladder dysfunction (e.g. in Parkinson's disease, spinal cord injury, stroke or multiple sclerosis patients), bladder spasms, urinary incontinence, urinary retention, hypertrophied bladder neck, voiding dysfunction, interstitial cystitis, vaginismus, endometriosis, pelvic pain, prostate gland enlargement (Benign Prostatic Hyperplasia), prostatodynia, prostate cancer and priapism;

dermatological disorders including hyperhidrosis (including axillary hyperhidrosis, palmar hyperhidrosis and Frey's syndrome), bromhidrosis, cutaneous cell proliferative disorders (including psoriasis), skin wounds and acne;

pain disorders including back pain (upper back pain, lower back pain), myofascial pain, tension headache, fibromyalgia, painful syndromes, myalgia, migraine, whiplash, joint pain, post-operative pain, pain not associated with a muscle spasm and pain associated with smooth muscle disorders;

inflammatory disorders including pancreatitis, neurogenic inflammatory disorders (including gout, tendonitis, bursitis, dermatomyositis and ankylosing spondylitis);

secretory disorders such as excessive gland secretions, mucus hypersecretion and hyperlacrimation, holocrine gland dysfunction;

respiratory disorders including rhinitis (including allergic rhinitis), COPD, asthma and tuberculosis;

hypertrophic disorders including muscle enlargement, masseteric hypertrophy, acromegaly and neurogenic tibialis anterior hypertrophy with myalgia;

articular disorders including tennis elbow (or epicondilytis of the elbow), inflammation of joints, coxarthrosis, hip osteoarthritis, rotator muscle cap pathology of the shoulder, rheumatoid arthritis and carpal tunnel syndrome;

endocrine disorders like type 2 diabetes, hyperglucagonism, hyperinsulinism, hypoinsulinism, hypercalcemia, hypocalcemia, thyroid disorders (including Grave's disease, thyroiditis, Hashimoto's thyroiditis, hyperthyroidism and hypothyroidism), parathyroid disorders (including hyperparathyroidism and hypoparathyroidism), Cushing's syndrome and obesity;

autoimmune diseases like systemic lupus erythemotosus;

proliferative diseases including paraganglioma tumors, prostate cancer and bone tumors;

traumatic injuries including sports injuries, muscle injuries, tendon wounds and bone fractures; and veterinary uses (e.g. immobilisation of mammals, equine colic, animal achalasia or animal muscle spasms)

Pharmaceutical compositions according to the invention can also be used for cosmetic treatments including cosmetic treatments of the following cosmetic disorders:

skin defects;

facial asymmetry;

wrinkles including glabellar frown lines and facial wrinkles;

downturned mouth;

hair loss; and body odours.

Preferably, pharmaceutical compositions according to the invention will be used for preparing medicaments intended to treat a disease/a condition/a syndrome chosen from the following:

ophtalmological disorders selected from the group consisting of blepharospasm, strabismus (including restrictive or myogenic strabismus), amblyopia, protective ptosis, therapeutic ptosis for corneal protection and upper eyelid retraction;

movement disorders selected from the group consisting of hemifacial spasm, torticollis, cerebral palsy spasticity of the child, spasticity of the adult in post-stroke, multiple sclerosis, traumatic brain injury or spinal cord injury patients, idiopathic focal dystonias, muscle stiffness, Writer's cramp, hand dystonia, VI nerve palsy, oromandibular dystonia, head tremor, tardive dyskinesia, tardive dystonia, occupational cramps (including musicians' cramp), facial nerve palsy, jaw closing spasm, facial spasm, synkinesia, tremor, primary writing tremor, myoclonus, stiff-person-syndrome, foot dystonia, facial paralysis, painful-arm-and-moving-fingers-syndrome, tic disorders, dystonic tics, Tourette's syndrome, neuromyotonia, trembling chin, lateral rectus palsy, dystonic foot inversion, jaw dystonia, Rabbit syndrome, cerebellar tremor, III nerve palsy, palatal myoclonus, akasthesia, muscle cramps, IV nerve palsy, freezing-of-gait, extensor truncal dystonia, post-facial nerve palsy synkinesis, secondary dystonia, off period dystonia, cephalic tetanus, myokymia and benign cramp-fasciculation syndrome;

otorhinolaryngological disorders selected from the group consisting of spasmodic dysphonia, hypersalivation, sialorrhoea, ear click, tinnitus, vertigo, Meniere's disease, cochlear nerve dysfunction, stuttering, cricopharyngeal dysphagia, bruxism, closure of larynx in chronic aspiration, vocal fold granuloma, ventricular dystonia, ventricular dysphonia, mutational dysphonia, trismus, snoring, voice tremor, aspiration, tongue protrusion dystonia, palatal tremor and laryngeal dystonia;

gastrointestinal disorders selected from the group consisting of achalasia, anal fissure, constipation, temperomandibular joint dysfunction, sphincter of Oddi dysfunction, sustained sphincter of Oddi hypertension, intestinal muscle disorders, puborectalis syndrome, anismus, pyloric spasm, gall bladder dysfunction, gastrointestinal or oesophageal motility dysfunction, diffuse oesophageal spasm, oesophageal diverticulosis and gastroparesis;

urogenital disorders selected from the group consisting of detrusor sphincter dyssynergia, detrusor hyperreflexia, neurogenic bladder dysfunction in Parkinson's disease, spinal cord injury, stroke or multiple sclerosis patients, bladder spasms, urinary incontinence, urinary retention, hypertrophied bladder neck, voiding dysfunction, interstitial cystitis, vaginismus, endometriosis, pelvic pain, prostate gland enlargement (Benign Prostatic Hyperplasia), prostatodynia, prostate cancer and priapism;

dermatological disorders selected from the group consisting of axillary hyperhidrosis, palmar hyperhidrosis, Frey's syndrome, bromhidrosis, psoriasis, skin wounds and acne;

pain disorders selected from the group consisting of upper back pain, lower back pain, myofascial pain, tension headache, fibromyalgia, myalgia, migraine, whiplash, joint pain, post-operative pain and pain associated with smooth muscle disorders;

inflammatory disorders selected from the group consisting of pancreatitis, gout, tendonitis, bursitis, dermatomyositis and ankylosing spondylitis;

secretory disorders selected from the group consisting of excessive gland secretions, mucus hypersecretion and hyperlacrimation and holocrine gland dysfunction;

respiratory disorders selected from the group consisting of non-allergic rhinitis, allergic rhinitis, COPD and asthma;

hypertrophic disorders selected from the group consisting of muscle enlargement, masseteric hypertrophy, acromegaly and neurogenic tibialis anterior hypertrophy with myalgia;

articular disorders selected from the group consisting of tennis elbow (or epicondilytis of the elbow), inflammation of joints, coxarthrosis, hip osteoarthritis, rotator muscle cap pathology of the shoulder, rheumatoid arthritis and carpal tunnel syndrome;

endocrine disorders selected from the group consisting of type 2 diabetes, hypercalcemia, hypocalcemia, thyroid disorders, Cushing's syndrome and obesity;

prostate cancer; and traumatic injuries selected from the group consisting of sports injuries, muscle injuries, tendon wounds and bone fractures;

or for performing cosmetic treatments wherein the cosmetic disorder to be treated is selected from the group consisting of:

skin defects;

facial asymmetry;

wrinkles selected from glabellar frown lines and facial wrinkles;

downturned mouth; and hair loss.

More preferably, pharmaceutical compositions according to the invention will be used for preparing medicaments intended to treat a disease/a condition/a syndrome chosen from the following:

ophtalmological disorders selected from the group consisting of blepharospasm and strabismus;

movement disorders selected from the group consisting of hemifacial spasm, torticollis, cerebral palsy spasticity of the child and arm or leg spasticity of the adult in post-stroke, multiple sclerosis, traumatic brain injury or spinal cord injury patients;

otorhinolaryngological disorders selected from the group consisting of spasmodic dysphonia, hypersalivation, sialorrhoea, cricopharyngeal dysphagia, bruxism, closure of larynx in chronic aspiration, ventricular dystonia, ventricular dysphonia, mutational dysphonia, trismus, snoring, voice tremor, tongue protrusion dystonia, palatal tremor and laryngeal dystonia;

gastrointestinal disorders selected from the group consisting of achalasia, anal fissure, constipation, temperomandibular joint dysfunction, sphincter of Oddi dysfunction, sustained sphincter of Oddi hypertension, intestinal muscle disorders, anismus, pyloric spasm, gall bladder dysfunction, gastrointestinal or oesophageal motility dysfunction and gastroparesis;

urogenital disorders selected from the group consisting of detrusor sphincter dyssynergia, detrusor hyperreflexia, neurogenic bladder dysfunction in Parkinson's disease, spinal cord injury, stroke or multiple sclerosis patients, bladder spasms, urinary incontinence, urinary retention, hypertrophied bladder neck, voiding dysfunction, interstitial cystitis, vaginismus, endometriosis, pelvic pain, prostate gland enlargement (Benign Prostatic Hyperplasia), prostatodynia, prostate cancer and priapism;

dermatological disorders selected from the group consisting of axillary hyperhidrosis, palmar hyperhidrosis, Frey's syndrome, bromhidrosis, psoriasis, skin wounds and acne;

pain disorders selected from the group consisting of upper back pain, lower back pain, myofascial pain, tension headache, fibromyalgia, myalgia, migraine, whiplash, joint pain, post-operative pain and pain associated with smooth muscle disorders;

inflammatory disorders selected from the group consisting of pancreatitis and gout;

hyperlacrimation;

respiratory disorders selected from the group consisting of non-allergic rhinitis, allergic rhinitis, COPD and asthma;

masseteric hypertrophy;

articular disorders selected from the group consisting of tennis elbow (or epicondilytis of the elbow), inflammation of joints, coxarthrosis, hip osteoarthritis, rotator muscle cap pathology of the shoulder, rheumatoid arthritis and carpal tunnel syndrome;

obesity;

traumatic injuries selected from the group consisting of muscle injuries, tendon wounds and bone fractures;

or for performing cosmetic treatments wherein the cosmetic disorder to be treated is selected from the group consisting of:

skin defects;

facial asymmetry;

wrinkles selected from glabellar frown lines and facial wrinkles;

downturned mouth; and hair loss.

In a particularly preferred manner, pharmaceutical compositions according to the invention will be used for preparing medicaments intended to treat a disease/a condition/a syndrome chosen from the following: blepharospasm, hemifacial spasm, torticollis, cerebral palsy spasticity of the child and arm or leg spasticity of the adult in post-stroke, multiple sclerosis, traumatic brain injury or spinal cord injury patients, axillary hyperhidrosis, palmar hyperhidrosis, Frey's syndrome, skin wounds, acne, upper back pain, lower back pain, myofascial pain, migraine, tension headache, joint pain, tennis elbow (or epicondilytis of the elbow), inflammation of joints, coxarthrosis, hip osteoarthritis, rotator muscle cap pathology of the shoulder, muscle injuries, tendon wounds and bone fractures;

or for performing cosmetic treatments wherein the cosmetic disorder to be treated is selected from the group consisting of:

skin defects;

facial asymmetry; and wrinkles selected from glabellar frown lines and facial wrinkles.

The dose of botulinum neurotoxin complex (type A, B, C, D, E, F or G) or high purity botulinum neurotoxin (type A, B, C, D, E, F or G) which shall be needed for the treatment of the diseases/disorders mentioned above varies depending on the disease/disorder to be treated, administration mode, age and body weight of the patient to be treated and health state of the latter, and it is the treating physician or veterinary that will eventually make the decision. Such a quantity determined by the treating physician or veterinary is called here "therapeutically efficient quantity".

For botulinum neurotoxin complex (type A, B, C, D, E, F or G) or high purity botulinum neurotoxin (type A, B, C, D, E, F or G), this therapeutically efficient dose is often expressed as a function of the corresponding $LD_{50}$. By $LD_{50}$ should be understood in the present application the median intraperitoneal dose in mice injected with botulinum neurotoxin complex (type A, B, C, D, E, F or G) or high purity botulinum neurotoxin (type A, B, C, D, E, F or G) that causes death of half of said mice within 96 hours.

The term "about" refers to an interval around the considered value. As used in this patent application, "about X" means an interval from X minus 10% of X to X plus 10% of X, and preferably an interval from X minus 5% of X to X plus 5% of X.

Unless they are defined differently, all the technical and scientific terms used here have the same meaning as that usually understood by an ordinary specialist in the field to which this invention belongs. Similarly, all publications, patent applications, all patents and all other references mentioned here are incorporated by way of reference.

The following examples are presented by way of illustration and should in no way be considered to limit the scope of the invention.

EXAMPLES

Example 1

A Liquid Pharmaceutical Composition Containing the Following Components is Prepared

| | |
|---|---|
| *Clostridium botulinum* type A1 neurotoxin complex | 2,000 $LD_{50}$ units/ml |
| Sucrose | 11.7 mM |
| Histidine | 10 mM |
| Sodium chloride | 0.3 M |
| Polysorbate 80 | 0.01% v/v |
| pH | 6.5 |

The mixture containing nominally 2,000 $LD_{50}$ units of botulinum toxin per ml is lyophilised in a sterilised vial, which is then sealed. The solid composition obtained is stable for at least 18 months when stored at a temperature between 2 and 8° C. and at least 6 months at 23 to 27° C.

Example 2

A Liquid Pharmaceutical Composition Containing the Following Components is Prepared

| | |
|---|---|
| *Clostridium botulinum* type A1 neurotoxin complex | 500 $LD_{50}$ units/ml |
| Sucrose | 11.7 mM |
| Histidine | 10 mM |
| Sodium chloride | 0.3 M |
| Polysorbate 80 | 0.01% v/v |
| PH | 6.5 |

The liquid composition thus prepared is sealed in a syringe type device with no liquid/gaseous interface. Stored in these conditions, it is stable for at least six months at 23 to 27° C. and at least twelve months at 2-8° C.

Example 3

A Liquid Pharmaceutical Composition Containing the Following Components is Prepared

| | |
|---|---|
| *Clostridium botulinum* type A1 neurotoxin complex | 500 $LD_{50}$ units/ml |
| Sucrose | 11.7 mM |
| Histidine | 10 mM |
| Sodium chloride | 0.15 M |
| Polysorbate 80 | 0.01% v/v |
| PH | 6.5 |

The liquid composition composition thus prepared is sealed in a syringe type device with no liquid/gaseous interface. Stored in these conditions, it is stable for at least six months at 23 to 27° C. and at least twelve months at 2-8° C.

Analytical Methods

Mouse Toxicity Assay

A mouse toxicity assay can be used to measure the toxicity of botulinum neurotoxin complex (type A, B, C, D, E, F or G) or high purity botulinum neurotoxin (type A, B, C, D, E, F or G). In the assay, a standard diluent will be used to prepare a range of dilutions at or about the estimated $LD_{50}$ value. The range and scale of dilutions is arranged so as to establish an accurate $LD_{50}$ value.

Mice are injected intraperitoneally with a known and standardised volume of diluted toxin. After 96 hours, the number of deaths and survivors in each dilution group will be recorded. The $LD_{50}$ value is the median dose which kills half of the injected animals within 96 hours.

A composition according to the invention is considered stable over a certain period of time if at least 70% of the initial toxicity is maintained over said period of time relative to a reference preparation.

The invention claimed is:

1. A liquid pharmaceutical composition consisting of
   (a) botulinum toxin complex type A,
   (b) 0.01% (v/v) POLYSORBATE 80 (polyoxyethylene (20) sorbitan monooleate),
   (c) 0.15 M sodium chloride,
   (d) 10 mM histidine to maintain the pH at 6.5,
   (e) 11.7 mM sucrose, and
   (f) sterile water.

2. The liquid pharmaceutical composition according to claim 1, wherein the concentration of the botulinum toxin complex type A is 500 $LD_{50}$ units.

3. The liquid pharmaceutical composition according to claim 1, wherein said composition is sealed in a syringe device with no liquid/gaseous interface.

4. A liquid pharmaceutical composition consisting of
   (a) 100 to 2,000 $LD_{50}$ units botulinum toxin complex type A,
   (b) 0.005% to 0.02% (v/v) POLYSORBATE 80 (polyoxyethylene (20) sorbitan monooleate),
   (c) 0.15 to 0.3 M sodium chloride,
   (d) 5 to 20 mM histidine to maintain the pH at 5.5 to 7.5,
   (e) 10 to 20 mM sucrose, and
   (f) sterile water.

* * * * *